United States Patent [19]
Gekhter et al.

[11] Patent Number: 5,488,751
[45] Date of Patent: Feb. 6, 1996

[54] INTERDENTAL TOOTHBRUSH

[75] Inventors: Vladimir Gekhter, Skokie; John Shimkus, Bolingbrook, both of Ill.

[73] Assignee: John O. Butler Company, Chicago, Ill.

[21] Appl. No.: 278,019

[22] Filed: Jul. 20, 1994

[51] Int. Cl.⁶ ........................................ A46B 9/04
[52] U.S. Cl. .................. 15/167.1; 15/143.1; 15/144.1; 15/172; 15/184; 15/206; 132/321
[58] Field of Search .............................. 15/143.1, 144.1, 15/167.1, 172, 184, 206; 132/218, 317, 320, 321; D4/104, 131

[56] References Cited

U.S. PATENT DOCUMENTS

| | | | |
|---|---|---|---|
| D. 173,852 | 1/1955 | Pope | D4/131 |
| 376,540 | 1/1888 | McQuide | 15/143.1 |
| 1,369,966 | 3/1921 | Cosens et al. | 15/143.1 |
| 1,513,556 | 10/1924 | Lucia | 15/206 |
| 1,963,360 | 6/1934 | Gibbin et al. | 15/167.1 |
| 2,094,240 | 9/1937 | Herrick et al. | 15/143.1 |
| 3,163,874 | 1/1965 | Bauer | 15/206 |
| 3,559,226 | 2/1971 | Burns | 15/167.1 |
| 4,222,143 | 9/1980 | Tarrson et al. | 15/105 |
| 4,387,479 | 6/1983 | Kigyos | 15/167.1 |
| 4,399,582 | 8/1983 | Ernest et al. | 15/167.1 |
| 4,679,272 | 7/1987 | Florence | 15/167.1 |
| 4,691,404 | 9/1987 | Tarrson et al. | 15/206 |
| 5,351,358 | 10/1994 | Larrimore | 15/143.1 |

FOREIGN PATENT DOCUMENTS

| | | | |
|---|---|---|---|
| 1044 | 3/1979 | European Pat. Off. | 15/167.1 |
| 63-3226 | 1/1988 | Japan . | |
| 63-3225 | 1/1988 | Japan . | |
| 6-70812 | 3/1994 | Japan | 15/167.1 |

*Primary Examiner*—Mark Spisich
*Attorney, Agent, or Firm*—Laff, Whitesel, Conte & Saret, Ltd.

[57] ABSTRACT

An interdental handle having a molded-in-place twisted wire brush that includes a handle having a generally tapered first portion of reduced cross-section at one end with a flexing and substantially resilient capability, and a second portion of a larger cross-section at an opposite end which is relatively rigid. A brush with a twisted wire stem includes a distal end embedded in at least the first portion of the handle and a proximal end projecting from the first portion of the handle. At least one concentric groove is adjacent the distal end of the twisted wire stem for preventing protrusion of the twisted wire stem from the first portion during the manufacturing process. The concentric groove includes a diameter which is substantially larger than the diameter of the twisted wire stem.

19 Claims, 2 Drawing Sheets

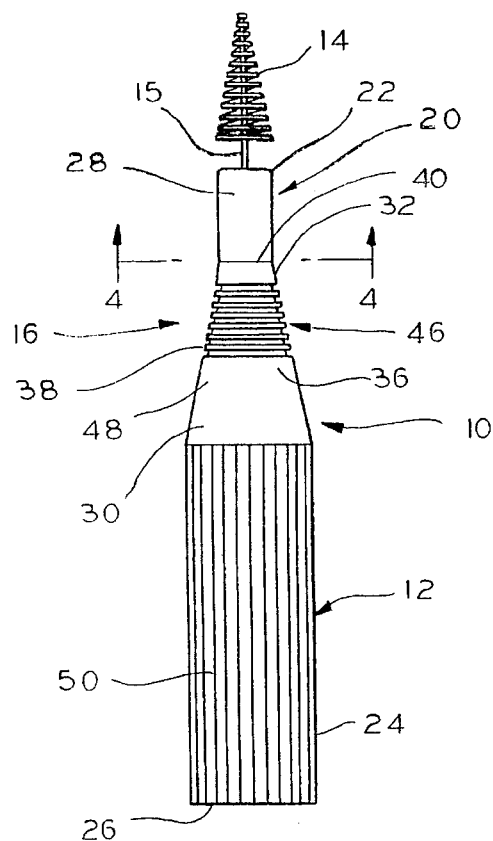
FIG.1
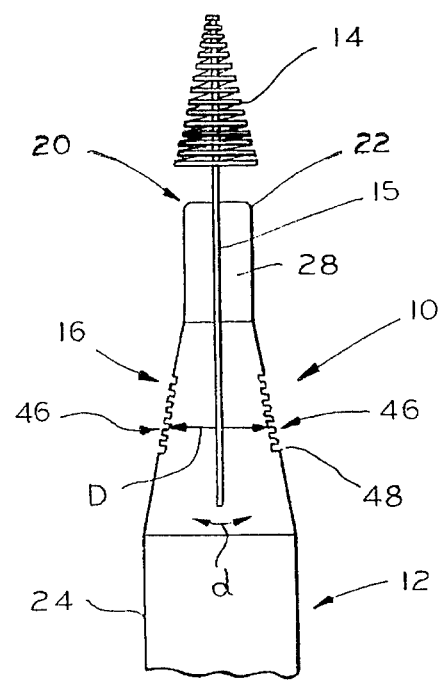
FIG.2
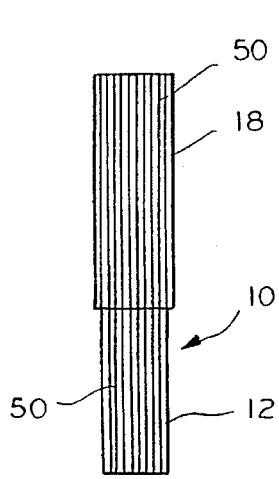
FIG.3
FIG.4
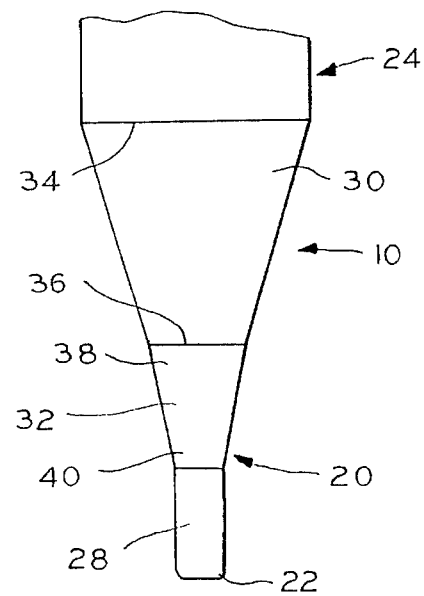
FIG.5

U.S. Patent    Feb. 6, 1996    Sheet 2 of 2    5,488,751
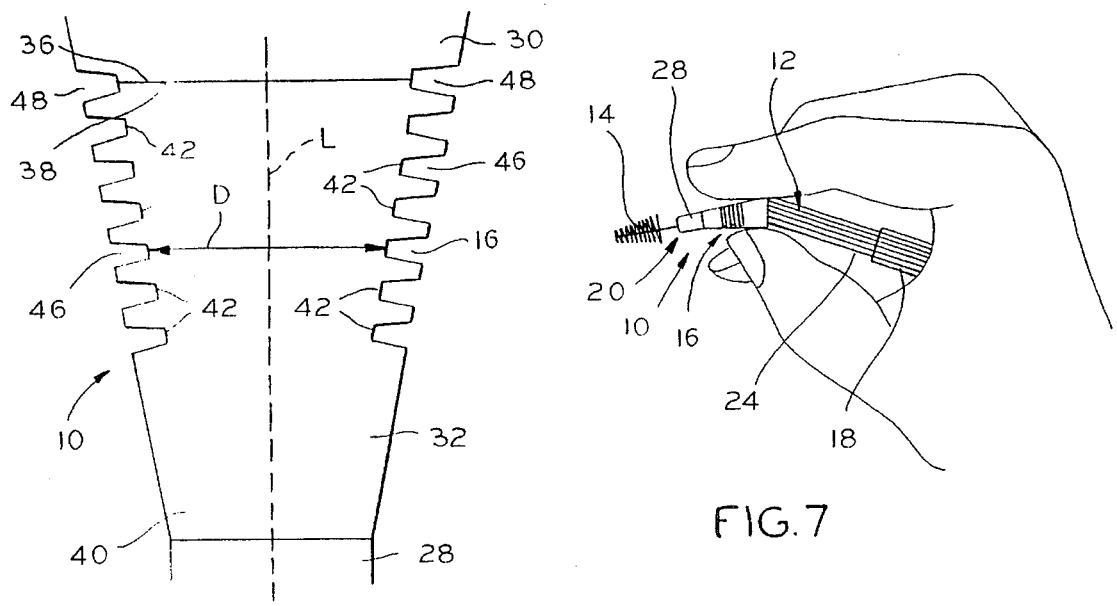
FIG. 6
FIG. 7
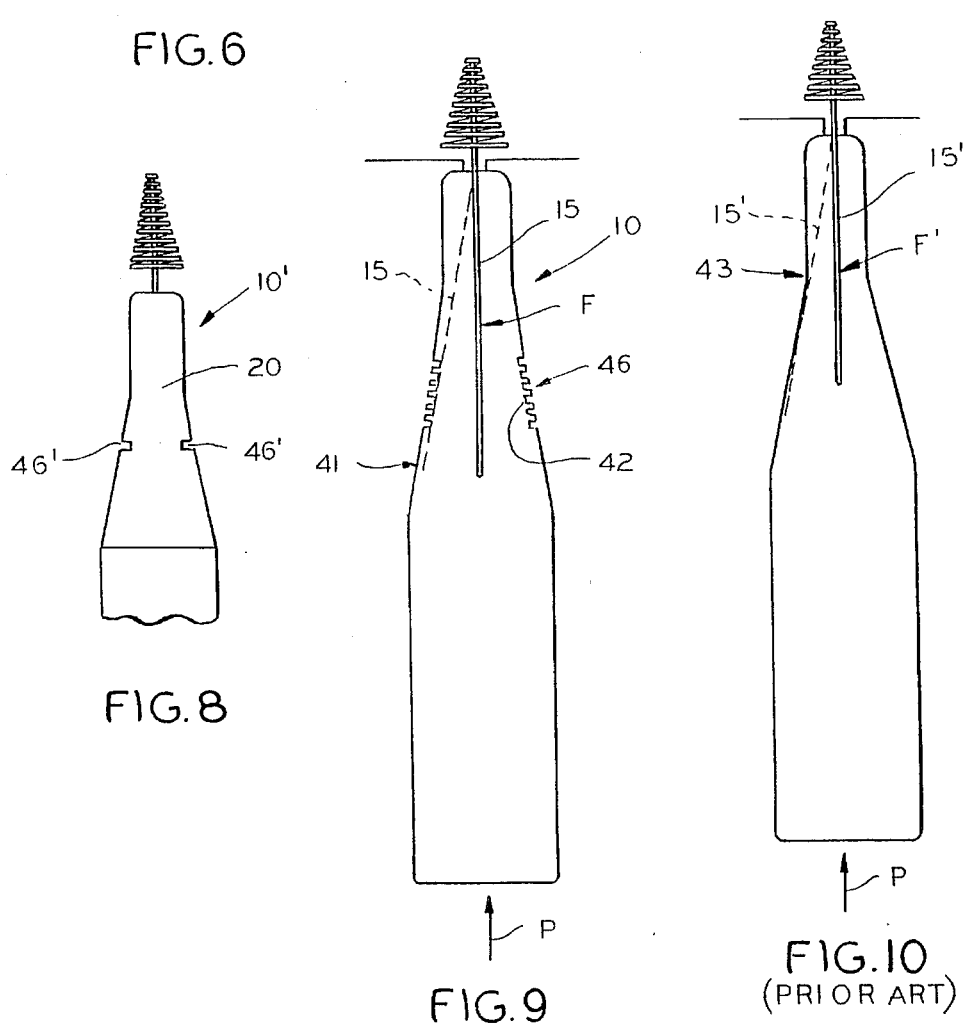
FIG. 8
FIG. 9
FIG. 10
(PRIOR ART)

5,488,751

INTERDENTAL TOOTHBRUSH

FIELD OF THE INVENTION

This invention relates to toothbrushes. More particularly, this invention relates to interdental toothbrushes which facilitate a more efficient and cost-effective manufacturing process.

BACKGROUND OF THE INVENTION

Interdental brush handles and brushes are well known in the dental industry, as described for example in U.S. Pat. Nos. 3,559,226, 4,222,143, and 4,387,479. Interdental brushes fit into spaces between and around the teeth and are generally used by people with special brushing needs such as, for example, people who wear dental bridges. Thus, a variety of interdental brush handles are available, including small, portable devices which fit easily into pockets or purses. These devices are generally rigid units with several pans that include handles, brushes integral with the handles, and often covers that slip over the brushes. However, the rigidity of prior art handles often interferes with the interdental cleaning process, particularly where visual contact is required. As a result, the rigid prior art interdental devices are generally inadequate for thorough or extensive interdental cleaning.

Thus, flexible, portable interdental brushes were introduced in an effort to decrease or eliminate problems associated with rigid devices. Two such flexible interdental brushes are shown in Japanese Utility Model Publications Nos. 63-3225 and 63-3226. In the first publication (63-3225), the interdental brash includes a bellowed portion of smaller cross-section which bifurcates the larger neck portion of the brush. The brush stem extends through the bifurcated neck and bellowed portion. The bellowed portion holds the brush stem and permits deflection of the stem to a desired angle. In the second publication (63-3226), the interdental brush includes a holding rod for holding a brush stem which is integrated with the handle of the brush. Both the holding rod and the brash stem may be deflected to a desired angle.

Another interdental brush is disclosed in U.S. Pat. No. 4,691,404. It includes a smooth, flexible tip end for easy access to the more remote or difficult to reach regions of the mouth. This interdental brush includes a selected amount of flexibility in the neck region at a junction between the handle and the brush stem which permits deflection of the neck to a desired brushing angle.

While the flexible interdental brush disclosed in U.S. Pat. No. 4,691,404 is effective in interdental cleaning, a problem sometimes arises during the manufacturing process of these brushes. The wire brush stem will sometimes protrude or become exposed along a side of the handle. This can occur during the injection molding process because the thin, flexible wire brush stems are molded under pressure into very narrow, tapered portions of the brush handles. The narrowness of these portions of the brush handles precludes any substantial movement of the wire brush stems within the handles without the resultant exposure of the wire stems. As a result, movement of the stems resulting from the pressure of the injection molding process must be carefully controlled. In addition, the tapered configuration of the brush handles contributes to the problems associated with exposed and protruding wire brush stems, especially in brush handles with varying angled or shaped sections. In such instances, the wire brush stems can become excessively exposed at the junction of the differently angled or shaped sections. Because interdental brushes with protruding wires may be unacceptable commercially, they must be discarded as waste thereby increasing scrap levels, labor, and operating costs in the manufacturing process.

Accordingly, an object of the present invention is to provide an interdental toothbrush which retains the functional characteristics of the brushes shown, for example, in U.S. Pat. No. 4,691,404, but which facilitates a more efficient and cost-effective manufacturing process.

It is another object of the present invention to provide a flexible interdental toothbrush which includes a plurality of concentric grooves for preventing undesirable protrusion of the twisted wire stem from the neck of the brush handle during the manufacturing process.

It is another object of the present invention to provide a flexible interdental toothbrush which includes sufficient spacing between the outer surface of the neck of the handle and the wire brush stem.

It is another object of the present invention to provide a flexible interdental toothbrush which reduces the scrap level during the manufacturing process and thereby reduces operating costs by substantially eliminating the sorting process for defective brushes.

Other objects and advantages of the invention will appear hereinafter.

SUMMARY OF THE INVENTION

The present invention in a preferred embodiment accomplishes the foregoing objects by providing an interdental toothbrush comprising a plastic handle with a molded-in-place twisted wire brush projecting from the handle in axial alignment therewith. The handle includes a first portion of reduced cross-section at one end with a flexing and substantially resilient capability, and a second portion of a larger cross-section at an opposite end which is relatively rigid. The twisted wire stem includes a distal end embedded in at least the first portion of the handle and a proximal end which projects from the first portion of the handle. A plurality of concentric grooves are provided in the neck of the handle adjacent the distant end of the twisted wire stem.

The first portion of the handle is generally tapered and includes a tip end, and a first and second truncated section which each have a lower plane and an upper plane. The lower plane of the first truncated section is integral with and adjacent the second portion, the lower plane of the second truncated section is integral with and adjacent the upper plane of the first truncated section, and the tip end is integral with the adjacent the upper plane of the second truncated section. The grooves are substantially located on the second truncated section of the first portion and are generally equidistant from one another.

The grooves include corresponding inner surfaces with diameters which are substantially larger than the diameter of the twisted wire stem for permitting lateral movement of the twisted wire stem towards the inner surfaces during the manufacturing process. The grooves extend from the base of the second truncated section towards the tip end, with the inner surfaces of the grooves being increasingly proximal to the central longitudinal axis of the second truncated section. One of the grooves is interposed between the lower plane of the second truncated section and the upper plane of the first truncated section of the first portion and includes a depth and a width which exceeds that of the other grooves. The interposed groove is preferably an end groove. In an alternate embodiment, there is a single circumferentially extending groove located on the first portion of the handle.

A cap is preferably provided on the interdental brush for covering the first portion and the brushing means and for receiving the second portion of the handle when the cap is removed from the first portion during use.

The inventive interdental brush is manufactured by an injection molding process which involves molding plastic around the twisted wire stem of the brush to form the body of the brush. The mold includes a cavity that is substantially conical at the base of the holder and substantially cylindrical at the top of the holder. A plurality of concentric grooves are formed on the conical cavity. A twisted wire stem is inserted through the base of the holder and into the center of the conical cavity. Plastic is introduced through the top of the holder and into the conical and cylindrical cavities. The pressure resulting from the introduction of the plastic forcibly moves the wire brash stem into juxtaposition with the inner surface of the concentric grooves on one side of the conical cavity while simultaneously spacing the twisted wire stem from the inner surface of the conical cavity.

Thus, the concentric grooves on the tapered portion of the brush handle maintain the twisted wire stem in juxtaposition with the inner surface of the grooves and prevent the twisted wire stem from projecting beyond the edges of the molded plastic handle during the manufacturing process. In addition, the larger diameter of the inner surfaces of the concentric grooves increases the space between the brush handle and the twisted wire stem which permits sufficient lateral movement of the wire stem within the conical cavity during the injection of the plastic into the mold. Consequently, the concentric grooves lower the number of defective brushes from as much as about 30% to as little as about 0% during the molding process. This is especially cost-effective in that a defect level of 30% requires the addition of a full-time employee to sort the defective brushes. Reducing the defect rate to the extent indicated saves labor and increases manufacturing efficiencies.

The above, as well as other objects and advantages of the invention, will become apparent from the following detailed description of the preferred embodiments, reference being made to the accompanying drawings.

BRIEF DESCRIPTION OF THE DRAWINGS

FIG. 1 is a side view of the inventive interdental toothbrush.

FIG. 2 is a partial side view of the toothbrush of FIG. 1.

FIG. 3 is a side view of the toothbrush of FIG. 1, illustrating its appearance when covered by the cap means.

FIG. 4 is a cross-sectional view of the toothbrush, taken along lines 4—4 of FIG. 1.

FIG. 5 is a partial side view of the body of the toothbrush of FIG. 1.

FIG. 6 is a partial view of the middle portion of the toothbrush of FIG. 1, illustrating the proximity of the concentric grooves from one another and from the central longitudinal axis of the toothbrush.

FIG. 7 is a perspective view of the toothbrush of FIG. 1, illustrating its appearance during use.

FIG. 8 is an alternate embodiment of the inventive toothbrush.

FIG. 9 is a cross-sectional side view of the toothbrush of FIG. 1, illustrating the movement of the twisted wire stem within the brush handle during the injection molding process.

FIG. 10 is a cross-sectional side view of a prior art interdental toothbrush, illustrating the exposure of the twisted wire stem along the side of the brush handle.

DETAILED DESCRIPTION OF THE INVENTION

Generally referring to FIGS. 1–3, the invention provides an interdental brash, denoted by the numeral 10, that comprises a handle 12, a brush 14 with a twisted wire stem 15, and a ripple neck 16 located on handle 12 for preventing undesirable protrusion of twisted wire stem 15 from the handle during the manufacturing process. In addition, a cap 18 covers a portion of handle 12 and brush 14. When the cap is removed, it may be attached to the handle end opposite the brush to extend the length of the toothbrush. Interdental brush 10 is manufactured from plastic by injection molding.

Handle 12 includes a first portion 20 of a reduced cross-section at one end 22 with a flexing and substantially resilient capability, and a second portion 24 of a larger cross-section at an opposite end 26 which is relatively rigid (FIGS. 1, 4). First portion 20 is generally tapered, whereas second portion 24 is generally cylindrical. First portion 20 is integral with second portion 24.

First portion 20 includes a tip end 28, and first and second truncated sections, 30 and 32, respectively (FIGS. 1, 5). First truncated section 30 includes a first lower plane 34 and a first upper plane 36 and, in one preferred embodiment, is about 0.2612 inches in length. In this embodiment, truncated section 30 is angled approximately 0.1082 inches from the vertical, as measured from first upper plane 36. Likewise, second truncated section 32 includes a second lower plane 38 and a second upper plane 40 and is about 0.1410 in length. Second truncated section 32 is angled approximately 0.90 inches from the vertical, as measured from the second upper plane 40. First lower plane 34 of first truncated section 30 is integral with and adjacent second portion 24. Similarly, second lower plane 38 of second truncated section 32 is integral with and adjacent first upper plane 36 of first truncated section 30. In addition, the bottom portion of tip end 28 is integral with and adjacent second upper plane 40 of second truncated section 32 and is approximately 0.1277 inches in length. Ripple neck 16 is located on part of the second truncated section 32 of first portion 20, and will be described in greater detail hereinafter.

Twisted wire stem 15 is flexible and is embedded in at least first portion 20 of handle 12 and projects from first portion 20 in axial alignment with the handle (FIGS. 1, 2). The diameter of the stem is designated as "d". Twisted wire stem 15 preferably extends substantially into second portion 24 (FIG. 2) and is embedded into the handle 12 by injection molding, as described below.

Ripple neck 16 is located on first portion 20 of handle 12 and prevents twisted wire stem 15 from protruding from the side of the handle during the manufacturing process (FIGS. 1, 2, 6). Ripple neck 16 preferably comprises a plurality of concentric and inwardly stepped grooves 46 which extend, in the illustrated embodiment, over approximately 0.0905 inches of first portion 20, as measured from lower plane 38 of second truncated section 32 towards tip end 28 (FIG. 6). In an alternate embodiment, there is a single circumferentially extending groove 46' on first portion 20 of handle 12 (FIG. 8).

Grooves 46 include corresponding inner surfaces 42, which are increasingly proximal to the central longitudinal axis L of second truncated section 32 as they extend towards tip end 28 (FIG. 6). The grooves adjacent lower plane 38 of second truncated section 32 include inner surfaces which are furthest from central longitudinal axis L of second truncated section 32. Specifically, in the illustrated embodiment, these grooves are approximately 0.0414 inches from axis L, as measured from the center of their inner surfaces. In contrast, the grooves nearest tip end 28 include inner surfaces which are in closest proximity to central longitudinal axis L of second truncated section 32 (approximately 0.0326 inches from axis L). The remaining grooves are positioned between the above-mentioned grooves and include inner surfaces which are each approximately 0.0370 inches from axis L.

In the preferred embodiment, one of grooves 46 is interposed between first upper plane 36 of first truncated section 30 and second lower plane 38 of second truncated section 32 of handle 12 (FIGS. 1, 6). Interposed groove 48 includes a depth and a width which exceeds that of the other grooves. Interposed groove 48 is preferably an end groove and includes a center which is approximately 0.0162 inches from the center of the adjacent groove. All other grooves are preferably equidistant from one another and measure approximately 0.0132 inches from center to center.

Grooves 46 further include diameters D that are substantially larger than diameter d of twisted wire stem 15 to permit lateral movement of the twisted wire stem towards the inner surfaces during the manufacturing process (FIGS. 2, 6).

Cap 18 covers first portion 20 and brushing means 14 (FIG. 3). When the cap is removed from first portion 20, it can be attached to second portion 24 of handle 12 to extend the length of the handle. Moreover, means (not shown) may be provided in cap 18 for limiting movement of first and second portions, 20 and 24, respectively, when they are inserted into the cap. The means are described in U.S. Pat. No. 4,691,404. In addition, longitudinal ribs 50 are provided on cap 18 and second portion 24 of handle 12 to, in part, give the cap and handle a better feel to the user (FIG. 3).

In use, tip end 28 of interdental brush 10 is held between the thumb and index finger of the user, while the opposite end of the handle is captured and stabilized along the length of the finger (FIG. 7). Alternatively, the brush may be captured in the fleshy fold of the palm if cap means 18 is positioned on second portion 24 of the handle. The index finger is then pressed against tip end 28 as handle 12 is held by the thumb for deflecting, bending, or flexing the brush at a desired angle. The brush is subsequently placed in the space between the teeth for cleaning.

Interdental brush 10 is manufactured by an injection molding process which involves molding plastic around twisted wire stem 15 of a wire brush holder to form the body of the brush. As previously mentioned, the process uses a mold that includes a cavity 41 that is substantially conical at the base of the holder and substantially cylindrical at the top of the holder. At least one, but preferably a plurality, of concentric grooves 46 are also formed along the inner surface 42 of the conical cavity. Wire brush stem 15 is inserted through the base of the holder and into the center of the conical cavity. Plastic is then introduced through the top of the holder into the conical and cylindrical cavities, as indicated by arrow P in FIG. 9. The resultant pressure from the injected plastic forces wire brush stem 15 into juxtaposition with inner surfaces 42 of concentric grooves 46 on one side of the conical cavity, as indicated by arrow F in FIG. 9. The juxtaposed twisted wire stem is likewise spaced from inner surfaces 42 of concentric grooves 46 on the diametrically opposite side of the conical cavity.

FIG. 10 shows a prior art interdental brush which lacks concentric grooves. As depicted in FIG. 10, the twisted wire stem 15' is moved by force F' to the outer edge of the brush handle wherein it is exposed along the side of the brush handle at junction 43 of the cylindrical tip end and the conical neck portion. Because most twisted wire stem exposure occurs along differently shaped or angled portions of interdental brushes, the absence of concentric grooves at the cylindrical-conical junction in the brush handle of FIG. 10 results in the protrusion of twisted wire stem 15' at the junction. Consequently, the brush handle of FIG. 10 must be discarded as waste.

The material from which interdental brush 10 is constructed preferably includes a mixture of a thermoplastic elastomer, polymer material and a polypropylene of a general purpose homopolymer grade but may include other comparable materials. Wire stem 15 may be made from heat-resistant and flexible metal material, suitable for use in the oral cavity. Moreover, although interdental brush 10 has been described in the terms of approximate measurements, as it should be understood that the dimensions of the brush may vary according to need.

Therefore, it should be recognized that, while the invention has been described in relation to a preferred embodiment thereof, those skilled in the art may develop a wide variation of structural details without departing from the principles of the invention. Accordingly, the appended claims are to be construed to cover all equivalents falling within the scope and spirit of the invention.

The invention claimed is:

1. An interdental handle having a molded-in-place twisted wire brush comprising:

a handle having a first portion at one end with a flexing and substantially resilient capability, and a second portion at an opposite end which is relatively rigid; and a brush with a twisted wire stem having a distal end embedded in at least said first portion of said handle and a proximal end projecting from said first portion of the handle;

said first portion including at least two integrally formed and differently shaped truncated sections, said first portion having at least one circumferentially extending groove located on one of said truncated sections adjacent the distal end of the twisted wire stem for preventing undesirable protrusion of the twisted wire stem from the first portion during manufacture of said interdental handle, said at least one circumferentially extending groove having a diameter which is substantially larger than the diameter of the twisted wire stem.

2. The interdental brush of claim 1 wherein said at least one circumferentially extending groove includes a corresponding inner surface, and said larger diameter of said at least one circumferentially extending groove permits the lateral movement of said twisted wire stem towards the inner surface of said at least one circumferentially extending groove during manufacture of said interdental handle.

3. The interdental brush of claim 1 wherein said first portion has multiple concentric grooves.

4. The interdental brush of claim 1 further comprising cap means for covering said first portion and said brush.

5. The interdental brush of claim 1 wherein said twisted wire stem is embedded into said first portion of the handle by injection molding.

6. An interdental handle having a molded-in-place twisted wire brush comprising:

a handle having a first portion at one end with a flexing and substantially resilient capability, and a second portion at an opposite end which is relatively rigid; and a brush with a twisted wire stem having a distal end embedded in at least said first portion of said handle and a proximal end projecting from said first portion of the handle;

said first portion having at least one circumferentially extending groove adjacent the distal end of the twisted wire stem for preventing undesirable protrusion of the twisted wire stem from the first portion during manufacture of said interdental handle, said at least one circumferentially extending groove having a diameter which is substantially larger than the diameter of the twisted wire stem, wherein said first portion is generally tapered and includes a tip end, and a first and second truncated section each having a lower plane and an upper plane, the lower plane of said first truncated section being integral with and adjacent said second portion, the lower plane of said second truncated section being integral with and adjacent said upper plane of said first truncated section, and said tip end being integral with and adjacent said upper plane of said second truncated section, said at least one circumferentially extending groove being substantially located on said second truncated section of said first portion.

7. An interdental handle having a molded-in-place twisted wire brush comprising:

a handle having a first portion at one end with a flexing and substantially resilient capability, and a second portion at an opposite end which is relatively rigid; and a brush with a twisted wire stem having a distal end embedded in at least said first portion of said handle and a proximal end projecting from said first portion of the handle;

said first portion including at least two integrally formed and differently shaped truncated sections, said first portion having a circumferentially extending ripple neck located on at least one of said truncated sections adjacent the distal end of the twisted wire stem for preventing protrusion of the twisted wire stem from the first portion during manufacture of said interdental handle, said ripple neck being substantially tapered.

8. The interdental brush of claim 7 wherein said ripple neck includes a diameter which is substantially larger than the diameter of the twisted wire stem.

9. The interdental brush of claim 8 wherein said ripple neck includes a corresponding inner surface, and said larger diameter of said ripple neck permits the lateral movement of said twisted wire stem towards the inner surface of said ripple neck during manufacture of said interdental handle.

10. The interdental brush of claim 7 further comprising cap means for covering said first portion and said brush.

11. The interdental brush of claim 7 wherein said twisted wire stem is embedded into said first portion of the handle by injection molding.

12. An interdental handle having a molded-in-place twisted wire brush comprising:

a handle having a first portion at one end with a flexing and substantially resilient capability, and a second portion at an opposite end which is relatively rigid; and a brush with a twisted wire stem having a distal end embedded in at least said first portion of said handle and a proximal end projecting from said first portion of said handle;

said first portion having a circumferentially extending ripple neck adjacent the distal end of the twisted wire stem for preventing protrusion of the twisted wire stem from the first portion during manufacture of said interdental handle, said ripple neck being substantially tapered, wherein said first portion includes a tip end, and a first and second truncated section each having a lower plane and an upper plane, the lower plane of said first truncated section being integral with and adjacent said second portion, the lower plane of said second truncated section being integral with and adjacent said upper plane of said first truncated section, and said tip end being integral with and adjacent said upper plane of said second truncated section, said ripple neck being substantially located on said second truncated section of said first portion.

13. The interdental brush of claim 12 wherein said ripple neck comprises a plurality of concentric grooves.

14. The interdental brush of claim 13, wherein said grooves include corresponding inner surfaces, and said grooves extend from the lower plane of said second truncated section towards said tip end, with said inner surfaces of said grooves being increasingly proximal to said second truncated section along its central longitudinal axis as they extend towards said tip end.

15. The interdental brush of claim 14 wherein said grooves are generally equidistant from one another.

16. An interdental handle having a molded-in-place twisted wire brush comprising:

a handle with a central longitudinal axis, said handle having a first portion of reduced cross-section at one end with a flexing and substantially resilient capability, and a second portion of a larger cross-section at an opposite end which is relatively rigid; and a brush with a twisted wire stem having a distal end embedded in at least said first portion of said handle and a proximal end projecting from said first portion of the handle;

said first portion having a plurality of circumferentially extending grooves adjacent the distal end of the twisted wire stem for preventing undesirable protrusion of the twisted wire stem from the first portion during manufacture of said interdental handle, each of said grooves having a corresponding inner surface, said twisted wire stem being juxtaposed against one side of said inner surface and being spaced from the opposite side of said inner surface, said sides of said inner surfaces being on diametrically opposite sides of said central longitudinal axis of said handle.

17. The interdental brush of claim 16 wherein said first portion is generally tapered and includes a tip end, and a first and second truncated section each having a lower plane and an upper plane, the lower plane of said first truncated section being integral with and adjacent said second portion, the lower plane of said second truncated section being integral with and adjacent said upper plane of said first truncated section, and said tip end being integral with and adjacent said upper plane of said second truncated section, said circumferentially extending grooves being substantially located on said second truncated section of said first portion.

18. The interdental brush of claim 17 wherein said grooves extend from the lower plane of said second truncated section towards said tip end, with said grooves being increasingly proximal to the central longitudinal axis of said second truncated section as they extend towards the tip end.

19. The interdental brush of claim 18 wherein said grooves are generally equidistant from one another.

* * * * *

UNITED STATES PATENT AND TRADEMARK OFFICE
CERTIFICATE OF CORRECTION

PATENT NO. : 5,488,751
DATED : February 6, 1996
INVENTOR(S) : Vladimir Gekhter It is certified that error appears in the above-identified patent and that said Letters Patent is hereby corrected as shown below:

Column 1, line 21, delete "pans" and insert --parts--.

Column 1, line 33, delete "brash" and insert --brush--.

Column 1, line 41, delete "brash" and insert --brush--.

Column 3, line 3, delete "brash" and insert --brush--.

Column 3, line 10, delete "brash" and insert --brush--.

Column 3, line 18, delete "brash" and insert --brush--.

Column 4, line 10, delete "brash" and insert --brush--.

Claim 2, line 1, delete "brush" and insert --handle--.

Claim 3, line 1, delete "brush" and insert --handle--.

Claim 4, line 1, delete "brush" and insert --handle--.

Claim 5, line 1, deltse "brush" and insert --handle--.

UNITED STATES PATENT AND TRADEMARK OFFICE
CERTIFICATE OF CORRECTION

PATENT NO. : 5,488,751
DATED : February 6, 1996
INVENTOR(S) : Vladimir Gekhter

It is certified that error appears in the above-identified patent and that said Letters Patent is hereby corrected as shown below:

Claim 7, line 17, delete "tipple" and insert --ripple--.

Claim 8, line 1, delete "brush" and insert --handle--.

Claim 9, line 1, delete "brush" and insert --handle--;

line 3, delete "tipple" and insert --ripple--.

Claim 10, line 1, delete "brush" and insert --handle--.

Claim 11, line 1, delete "brush" and insert --handle--.

Claim 13, line 1, delete "brush" and insert --handle--.

Claim 14, line 1, delete "brush" and insert --handle--.

Claim 15, line 1, delete "brush" and insert --handle--.

Claim 17, line 1, delete "brush" and insert --handle--.

Claim 18, line 1, delete "brush" and insert --handle--.

UNITED STATES PATENT AND TRADEMARK OFFICE
CERTIFICATE OF CORRECTION

PATENT NO. : 5,488,751
DATED : February 6, 1996
INVENTOR(S) : Vladimir Gekhter

It is certified that error appears in the above-identified patent and that said Letters Patent is hereby corrected as shown below:

Claim 19, line 1, delete "brush" and insert --handle--.

Signed and Sealed this

Twenty-first Day of April, 1998

Attest:

BRUCE LEHMAN

Attesting Officer    Commissioner of Patents and Trademarks